(12) United States Patent
Sapoznikov et al.

(10) Patent No.: US 9,457,131 B2
(45) Date of Patent: Oct. 4, 2016

(54) APPARATUS AND METHOD FOR PRODUCING A DENTAL BONE GRAFT

(71) Applicant: KometaBio Inc., Cresskill, NJ (US)

(72) Inventors: Lari Sapoznikov, Tel-Aviv (IL); Itzhak Binderman, Tel-Aviv (IL); Meir Sahar, Holon (IL)

(73) Assignee: KometaBio Inc., Cresskill, NJ (US)

( * ) Notice: Subject to any disclaimer, the term of this patent is extended or adjusted under 35 U.S.C. 154(b) by 0 days.

(21) Appl. No.: 14/419,691

(22) PCT Filed: Jan. 14, 2014

(86) PCT No.: PCT/IL2014/050037
§ 371 (c)(1),
(2) Date: Feb. 5, 2015

(87) PCT Pub. No.: WO2014/111925
PCT Pub. Date: Jul. 24, 2014

(65) Prior Publication Data
US 2015/0190549 A1    Jul. 9, 2015

Related U.S. Application Data

(60) Provisional application No. 61/752,453, filed on Jan. 15, 2013.

(51) Int. Cl.
*B02C 19/00* (2006.01)
*A61L 27/36* (2006.01)
(Continued)

(52) U.S. Cl.
CPC .......... *A61L 27/3691* (2013.01); *A61C 8/0006* (2013.01); *A61K 35/32* (2013.01);
(Continued)

(58) Field of Classification Search
CPC ............................ B02C 19/00; B02C 19/0056
USPC ............................ 241/199.12, 100, 282.1, 69
See application file for complete search history.

(56) References Cited

U.S. PATENT DOCUMENTS 3,089,652 A * 5/1963 Haber .................. A47J 43/046
241/282.1
5,240,187 A * 8/1993 Wilson .................... A61L 11/00
241/199.12
(Continued)

FOREIGN PATENT DOCUMENTS

JP    61287459 A  * 12/1986
KR    10-1175051    8/2012
(Continued)

OTHER PUBLICATIONS

International Preliminary Report on Patentability Dated Jul. 30, 2015 From the International Bureau of WIPO Re. Application No. PCT/IL2014/050037.

(Continued)

*Primary Examiner* — Mark Rosenbaum

(57) ABSTRACT

According to some embodiments of the invention, there is provided a method of producing a bone graft, comprising: providing a tooth, converting the tooth into a plurality of particles, and selecting from available particles a subset of particles. In some embodiments, the method is performed at a dental clinic. In some embodiments, the dental bone graft is an autograft produced by grinding a patient's tooth. According to some embodiments of the invention, there is provided an apparatus configured for connecting to a motor unit to produce a bone graft at a dental clinic, comprising: a housing encasing: a chamber sized to receive a tooth, a blade assembly positioned within the chamber and configured to pulverize the tooth, an accessible compartment in which a subset of tooth particles is collected, and one or more sieves positioned to sift particles that flow between the chamber and the accessible compartment.

31 Claims, 12 Drawing Sheets

(51) Int. Cl.
    *A61K 35/32*   (2015.01)
    *A61L 27/02*   (2006.01)
    *A61C 8/02*    (2006.01)
    *A61L 27/54*   (2006.01)
    *B02C 23/16*   (2006.01)

(52) U.S. Cl.
    CPC .......... *A61L 27/025* (2013.01); *A61L 27/3604* (2013.01); *A61L 27/365* (2013.01); *A61L 27/3608* (2013.01); *A61L 27/3641* (2013.01); *A61L 27/3683* (2013.01); *A61L 27/54* (2013.01); *B02C 19/00* (2013.01); *B02C 19/0056* (2013.01); *B02C 23/16* (2013.01); *A61L 2430/02* (2013.01); *A61L 2430/12* (2013.01)

(56) References Cited

U.S. PATENT DOCUMENTS

| | | | |
|---|---|---|---|
| 6,824,087 | B2 | 11/2004 | McPherson et al. |
| 2004/0202984 | A1 | 10/2004 | Kim et al. |
| 2007/0164137 | A1 | 7/2007 | Rasekhi |

FOREIGN PATENT DOCUMENTS

| | | |
|---|---|---|
| KR | 10-1326609 | 11/2013 |
| WO | WO 2014/111925 | 7/2014 |

OTHER PUBLICATIONS

International Search Report and the Written Opinion Dated May 11, 2014 From the International Searching Authority Re. Application No. PCT/IL2014/050037.

Kim et al. "A Comparison of Bone Generation Capability in Rabbits Using Tooth Ash and Plaster of Paris With Platelet-Rich Plasma or Fibrin Sealant", Oral Surgery, Oral Medicine, Oral Pathology, Oral Radiology, and Endodontology, 110(3): e8-e14, Sep. 2010.

Kim et al. "Autogenous Teeth Used for Bone Grafting: A Comparison With Traditional Grafting Materials", Oral Surgery, Oral Medicine, Oral Pathology, Oral Radiology, and Endodontology, 117(1): e39-e45, Jan. 2014.

Kim et al. "Combined Implantation of Particulate Dentine, Plaster of Paris, and A Bone Xenograft (Bio-Oss®) for Bone Regeneration in Rats", Journal of Cranio-Maxillofacial Surgery, 29: 282-288, 2001.

Kim et al. "Development of a Novel Bone Grafting Material Using Autogenous Teeth", Oral Surgery, Oral Medicine, Oral Pathology, Oral Radiology, and Endodontology, 109(4): 496-503, Apr. 2010.

Korea Dental Solution "BonMaker—BonMaker Is An Advanced System for Processing Patient's Teeth Into for 'Auto-Teeth Bone' Particulate Material", Korea Dental Solution Co., Ltd., Catalog, 2 P.

* cited by examiner

APPARATUS AND METHOD FOR PRODUCING A DENTAL BONE GRAFT

RELATED APPLICATION/S

This application is a National Phase of PCT Patent Application No. PCT/IL2014/050037 having International filing date of Jan. 14, 2014, which claims the benefit of priority under 35 USC §119(e) of U.S. Provisional Patent Application No. 61/752,453 filed on Jan. 15, 2013 The contents of the above applications are all incorporated herein by reference as if fully set forth in their entirety.

FIELD AND BACKGROUND OF THE INVENTION

The present invention, in some embodiments thereof, relates to a dental bone graft, and, more particularly, but not exclusively, to producing a dental bone graft at a dental clinic.

U.S. Pat. No. 6,824,087 B2 to McPherson et al., discloses "A bone mill for use in a surgical or otherwise sterile environment includes a particle reducer such as a pulverizing blade, a motor such as an electrical motor, and a coupling such as a rotary shaft for connecting the particle reducer to the motor."

SUMMARY OF THE INVENTION

According to an aspect of some embodiments of the invention there is provided a method of producing a bone graft, comprising: providing a tooth, converting the tooth into a plurality of particles, selecting from available particles a subset of particles. Optionally, the method is performed at a dental clinic. In some embodiments, a minimal diameter of at least 85% of the particles of the subset of particles is substantially 200 μm or more. In some embodiments, a maximal diameter of at least 85% of the particles of the subset of particles is substantially 1200 μm or less. In some embodiments, the method further comprises placing the selected subset of particles in a human jaw to act as a bone graft. In some embodiments, converting, selecting and placing is performed within a time limit of 30 minutes. In some embodiments, providing comprises providing a tooth extracted from the human jaw. In some embodiments, converting comprises pulverizing the tooth into the plurality of particles. In some embodiments, selecting comprises sifting the plurality of particles to receive particles having a size suitable for implanting as a bone graft. In some embodiments, sifting comprises vibrating at least one of: one or more sieves used for selecting of particles, a housing of a device in which the converting and selecting is performed, and the particles themselves. In some embodiments, selecting comprises sifting the plurality of particles in two stages, a first stage to remove particles having a size too large to be implanted as a bone graft, and a second stage to remove, out of particles that passed the first sifting stage, particles that are too small to be implanted as a bone graft. In some embodiments, the method further comprises automatically collecting the subset of particles in a container, and adding treatment fluid to the container. In some embodiments, the treatment fluid is sterilizing fluid suitable for removing organic debris from the subset of particles. In some embodiments, the method further comprises consolidating the particles. In some embodiments, the method further comprises drying the particles. In some embodiments, converting comprises converting dentin portions of the tooth into particles.

In some embodiments, the method further comprises storing the selected particles for future use. In some embodiments, converting comprises grinding, and selecting comprises vibrating.

According to an aspect of some embodiments of the invention there is provided an apparatus configured for connecting to a motor unit to produce a bone graft at a dental clinic, comprising: a housing encasing: a chamber sized to receive a tooth; a blade assembly positioned within the chamber and configured to pulverize the tooth; an accessible compartment in which a subset of tooth particles is collected; and one or more sieves positioned to sift particles that flow between the chamber and the accessible compartment. In some embodiments, the apparatus comprises two sieves: a first sieve sized to pass particles having a diameter which is substantially smaller than a first threshold, and a second sieve sized to pass particles having a diameter which is substantially smaller than a second threshold. Optionally, the first threshold is 1200 μm, and the second threshold is 200 μm. In some embodiments, particles passing through the first sieve are collected, and wherein particles passing through the second sieve are discarded. In some embodiments, the housing further comprises an additional compartment in which excess particles that are not suitable for use as a bone graft are collected. In some embodiments, the second sieve is positioned at an angle, forming a slanted surface on which the particles are advanced towards the accessible compartment. Optionally, the angle ranges between 3-40 degrees. In some embodiments, the second sieve is positioned within the accessible compartment in which particles that passed through the first sieve are collected. In some embodiments, the first sieve is configured vertically below the blades, and the second sieve is configured vertically below the first sieve, so that the flow of particles is driven by gravity. In some embodiments, the apparatus is packaged in a sealed container to maintain a sterile environment. In some embodiments, the apparatus is connected to a motor unit. In some embodiments, the apparatus is configured to attach to a connector for coupling the apparatus to the motor unit. Optionally, the connector is a rotary shaft. In some embodiments, the motor unit comprises a drive motor configured to move the blades. In some embodiments, at least one of the motor unit and the apparatus comprise a vibrating module configured to vibrate one or more of the sieves, the housing, or the particles. In some embodiments, at least one of the apparatus and a coupling between the apparatus and the motor unit is configured for preventing reuse of the apparatus. Optionally, the motor unit comprises a reader configured to recognize an identification code on the apparatus. Optionally, at least one of the motor unit and the apparatus comprises a breakable pin which prevents the apparatus from engaging the motor unit a second time. In some embodiments, the motor unit comprises circuitry configured for controlling parameters of at least one of pulverizing the tooth and sifting the particles. Optionally, the parameters comprise one or more of an RPM of the blades, an intensity of vibration of the sieves, a duration of grinding. In some embodiments, the circuitry is configured for providing a grinding mode and a vibration mode. In some embodiments, the motor unit further comprises a user interface configured as a button panel, for selecting the modes.

According to an aspect of some embodiments of the invention there is provided a kit for producing a bone graft at a dental clinic, to be used with a motor unit, comprising: an apparatus configured for converting a provided tooth into particles, and for selecting a subset of particles to be used as a bone graft; and at least one of: one or more treating solutions to be added to the subset of particles, and one or more teeth. Optionally, the teeth are cadaver teeth or porcine teeth. Optionally, the treating solution is a sterilizing solution.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
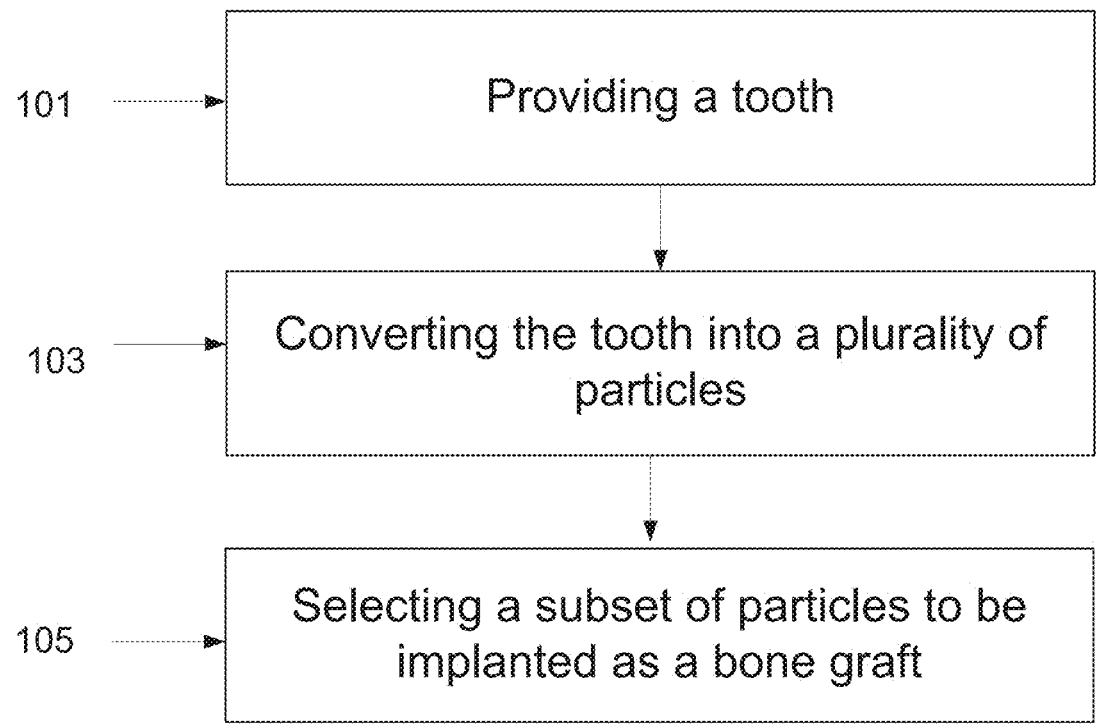
FIG. 1 is a flowchart of a general method for producing a dental bone graft, according to some embodiments of the invention.

The present invention, in some embodiments thereof, relates to a dental bone graft, and, more particularly, but not exclusively, to producing a dental bone graft from teeth, for example at a dental clinic.

An aspect of some embodiments of the invention relates to producing a bone graft from teeth. Optionally, the bone graft is produced at a dental clinic, for example by a dentist. In some embodiments, the bone graft is produced within, for example, 30 minutes from a time in which a tooth is provided. Optionally, the produced bone graft is implanted in a human jaw. In some embodiments, an extracted tooth of a patient is provided, and an autologous bone graft is produced from the tooth. Alternatively, a tooth such as a cadaver tooth or a porcine tooth is provided, and converted into a plurality of particles. Optionally, when implanted, the particulate form of the tooth matter, which acts as the graft, conforms to a shape of a recess or defect in a jaw bone. Optionally, one or more properties of the particulate tooth matter such as a chemical composition are similar to the properties of bone.

In some embodiments, converting the tooth into a plurality of particles includes pulverizing the tooth, for example grinding the tooth. In some embodiments, a subset of tooth particles is selected from the available particles. Optionally, the subset of particles is composed of particles having a certain size, for example substantially having a diameter ranging between a lower range of 100-400 µm, for example 150, 200, 250 µm or intermediate, larger or smaller lower range, and an upper range of 1000-1400 µm, such as 1200 µm, 1350 µm, or intermediate, larger or smaller. In one example, the subset of particles comprises at least 85%, 70%, 65%, 90%, 95% or intermediate, larger or smaller percentage of particles substantially having a diameter ranging between 200-1200 µm. In some embodiments, selecting is carried out by sifting the particles, for example using one or more sieves. Optionally, gradual sifting is performed, wherein two or more sifting stages are used, for example a first stage to remove particles that are too large to be used in and/or as a bone graft, and a second stage to remove particles that are too small. In some embodiments, the selected subset of particles is collected. Optionally, excess particles such as larger and/or smaller particles are collected. Optionally, the excess particles are disposed of. In some embodiments, the selected particles are prepared for implantation, for example processed by cleansing and/or sterilizing and/or drying and/or consolidating the particles. Optionally, the particles are prepared for storing for future use. In some embodiments, the process is repeated, for example for refining the selected particles.

An aspect of some embodiments of the invention relates to an apparatus configured to be coupled to a motor unit, to produce a bone graft. In some embodiments, the apparatus and motor unit are configured a as a table-top device, to be positioned, for example, at a dental clinic. In some embodiments, the apparatus is disposable.

In some embodiments, the apparatus comprises a grinding module, for example including a blade assembly comprising one or more blades suitable for pulverizing the tooth. In some embodiments, the apparatus is configured for selecting a subset of particles out of the ground particles, for example by comprising one or more sieves. Optionally, the sieves are formed with varying geometries, for example with openings having different diameters, for example a first sieve sized to let particles smaller than 1200 µm, 1000 µm, 900 µm in diameter or intermediate, larger or smaller diameters to pass through, and a second sieve sized to let particles smaller than 200 µm, 100 µm, 300 µm in diameter or intermediate, larger or smaller diameters to pass through. In some embodiments, the apparatus comprises a compartment in which the selected subset of particles is automatically collected. Optionally, the compartment is accessible to a user, to enable collection of the subset of particles to be used as a bone graft. Optionally, processing of the particles, for example by adding a treating solution such as a sterilizing solution, is performed within a container of the collection compartment. Optionally, one or more additional compartments are provided, for example a compartment in which excess particles are collected. In some embodiments, the grinding module, the one or more sieves, and/or the collection compartments are enclosed within a housing. Optionally, the housing comprises a lid to maintain a closed environment during operation.

In some embodiments, the apparatus is coupled to a motor unit. Optionally, the motor unit is configured for repetitive use, and the disposable apparatus is replaced, for example, between processing of different teeth and/or between patients. In some embodiments, a connector, for example in the form of a rotary shaft, couples between the motor unit and the apparatus. In some embodiments, the motor unit includes a drive motor configured for activating the grinding module, for example by rotating one or more blades of the blade assembly. In some embodiments, the motor unit and/or the apparatus comprises a vibrating module, for example a vibrating motor. Optionally, the drive motor is configured for vibrating. Optionally, the vibrating module is coupled to the one or more sieves. Additionally or alternatively, the vibrating module is coupled to the housing. Additionally or alternatively, the vibrating module is configured to cause vibration of the particles themselves. A potential advantage of vibration may include accelerating a sifting rate of the particles. In some embodiments, the one or more sieves are rotatable, for example by a drive motor. Optionally, a drive motor is configured for rotating the blades as well as the sieves.

In some embodiments, the motor unit comprises circuitry configured for controlling operational parameters. In some embodiments, the circuitry is configured for providing one or more operational modes, for example a grinding mode, a vibrating mode. Optionally, operational parameters such as a speed of rotation of the blades, an intensity of vibration, a duration of grinding are controlled by the circuitry. In some embodiments, the motor unit comprises a user interface, for example configured as a button panel. Optionally, the buttons provide functions such as activation of grinding, activation of sifting, mode selection, time selection, or other settings.

In some embodiments, the use of the disposable apparatus is limited. In some embodiments, a mechanism is employed to limit use of the disposable unit, for example, providing the processing of a single tooth only. In one example, the disposable unit comprises an identification code, which is recognized by a reader within the motor unit, allowing limited use. In another example, a breakable pin is positioned between the disposable unit and the motor unit, such that when coupled to each other the pin breaks, preventing engagement of the same disposable unit to the motor unit a second time. Optionally, the pin is a connecting element between the blade assembly and the motor unit. Optionally, the pin aligns between the disposable unit and the motor unit.

In some embodiments, a kit is provided, for example to a dental clinic. In some embodiments, the kit comprises a motor unit and one or more disposable units to be coupled to the motor unit. Alternatively, the kit does not include the motor unit. Optionally, the kit includes one or more treating solutions, such as sterilizing solutions. Optionally, the kit includes one or more teeth, such as Porcine teeth or cadaver teeth, to be converted into a bone graft. Optionally, the kit includes a hot plate for drying the produced particles. Alternatively, the kit includes a bone mill device, for example as taught in U.S. Pat. No. 6,824,087 to McPherson et al., and one or more teeth to be converted into a bone graft.

In some embodiments, methods and/or apparatuses for example as described herein can be used for bone graft production for applications other than dental, for example, producing a bone graft to implanted in orthopedic treatments, spinal treatments, or other transplants. In some embodiments, apparatuses for example as described herein are configured for receiving a bone, producing a subset of bone particles, and/or producing a graft from a bone.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a flowchart of a general method for producing a dental bone graft, according to some embodiments of the invention.

In some embodiments, the bone graft is produced from a tooth (101), for example a human tooth or porcine tooth. In some embodiments, the provided tooth is a tooth extracted from a patient.

In some embodiments, the tooth is converted into a plurality of particles (103). Optionally, converting includes breaking the tooth into smaller pieces, for example by grinding the tooth.

In some embodiments, a subset of particles is selected from the available tooth particles. Optionally, particles are selected by size. For example, in some embodiments, the subset of particles includes particles having a diameter substantially ranging between 200-1200 µm, 150-900 µm, 500-1500 µm, or intermediate, higher or smaller ranges. In some embodiments, selecting comprises sifting the particles, for example to separate the subset of particles from excess particles, such as particles that are too large or too small to be used for a bone graft.

In some embodiments, the tooth particles comprise dentin. Optionally, a percentage of the dentin found in particles of a single tooth ranges between 85% to 97%, for example 88%, 92%, 96%. In some embodiments, the particles comprise enamel. In some embodiments, the particles comprise cementum. A potential advantage of converting a complete tooth into particles to be used in a bone graft may include producing a graft with chemical and/or physical properties that are similar to compact bone. In some embodiments, a total weight of the selected subset of particles is at least 70%, 80%, 90%, 95% or intermediate, larger, or smaller percentages of the original weight of the provided tooth.

In some embodiments, the selected subset is used as a bone graft. Optionally, the particles are prepared for use as a bone graft, for example by cleansing, sterilizing, drying, and/or consolidating the particles, as will be further described herein. Optionally, one or more substances such as antibiotics, bisphosphonates, blood (for example of the patient in which the graft is implanted) or blood components, materials for inducing bone growth, are added to the particles.

In some embodiments, the produced bone graft is implanted in a jaw of a patient. Optionally, the produced graft is used for augmentation, such as sinus augmentation or ridge augmentation. Additionally or alternatively, the produced graft is implanted to form a supporting basis for placing an implant. Optionally, the bone graft is placed to restore the edentulous area of a missing tooth. Additionally or alternatively, the produced graft is implanted to restore a natural shape of the bone. Additionally or alternatively, the produced graft is implanted to rebuild and/or straighten a damaged bone. Additionally or alternatively, the produced graft is implanted to compensate for bone loss, for example caused by dental remodeling procedures. In some embodiments, the produced graft is implanted to support bone defects adjacent natural teeth, such as periodontal defects, and/or to restore lost alveolar bone.

Figure 2:
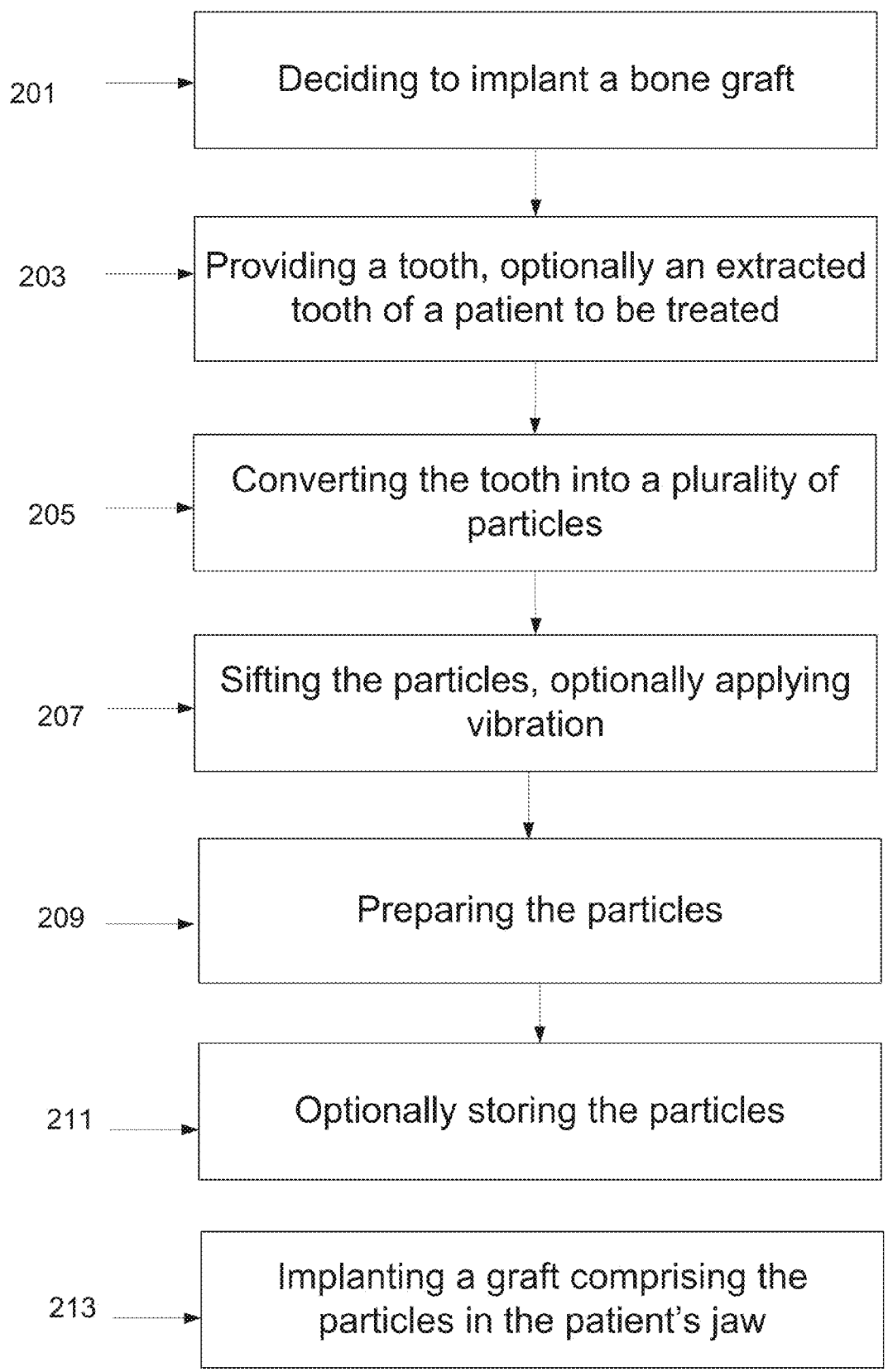
FIG. 2 is a flowchart of an exemplary procedure for treating a patient in need of a bone graft by producing a bone graft at a dental clinic, according to some embodiments of the invention.

FIG. 2 is a flowchart of an exemplary procedure for treating a patient in need of a bone graft by producing a bone graft at a dental clinic, according to some embodiments of the invention.

In some embodiments, a decision is made to implant a bone graft (201), for example in a patient's jaw. Optionally, the decision is made by a dentist.

In some embodiments, a tooth is provided (203). Optionally, the tooth was extracted from the patient to be treated. Optionally, the tooth was extracted, for example, two months, 1 month, 2 weeks, 1 day, 1 hour, 30 minutes or intermediate, longer or shorter time periods before the procedure. Additionally or alternatively, the tooth is a cadaver tooth. Additionally or alternatively, the tooth is an animal tooth, for example porcine tooth.

In some embodiments, the provided tooth was not treated prior to extraction, for example filled with material. Alternatively, if the tooth was treated prior to extraction, the tooth is processed to remove toxins or other materials not suitable for implantation. For example, toxins are removed by a cleanser.

In some embodiments, the tooth is converted into a plurality of particles (205). Optionally, the tooth is converted into a plurality of particles. Optionally, the tooth is converted into particles by grinding, crushing, cutting, and/or milling the tooth. In some embodiments, the tooth is broken into portions, and optionally these portions are further reduced in size into particles.

In some embodiments, the plurality of tooth particles are sifted (207). Optionally, the particles are passed through one or more sieves. In an example, two sieves are used for selecting a subset of particles to be used as a bone graft. Optionally, a first set of particles passes through a first sieve. Optionally, the first set is sifted again, and a second set of particles passes through a second sieve. Optionally, remaining particles of the first set which did not pass through the second sieve are selected for use as a bone graft. Optionally, the second set of particles (that passed through the second sieve) are too small to be used as a bone graft, and are optionally discarded. Alternatively, particles that passed through the second sieve are selected for use as a bone graft. Optionally, particles that did not pass through the first sieve are too large to be used as a bone graft, and are optionally discarded. Alternatively, the particles are selected for use a bone graft. Alternatively, the large particles are re-ground to reduce their size.

In some embodiments, sifting is carried out with the aid of gravitational forces, causing the particles to pass between the sieves. Optionally, the passing of particles is accelerated, using, for example, a flow or air or fluid. In some embodiments, vibration is applied, for example to the one or more sieves. Optionally, vibration increases the sifting rate. In some embodiment, sifting is performed within, for example, 10 seconds, 5 seconds, 30 seconds, or intermediate, longer or shorter time periods.

In some embodiments, the particles are prepared for use as a bone graft (209), for example as further explained hereinbelow in FIG. 3.

Optionally, the prepared particles are stored, for example for future use. Optionally, the particles are stored for a time period ranging between, for example, 1 day to 5 years, 1 hour to 2 days, 1 month to 3 months, 1 year to 10 years, or intermediate, longer or shorter ranges. Optionally, the particles are fully dried before storage. In some embodiments, the prepared particles are implanted as a bone graft (213), for example in the jaw bone of a patient. In some embodiments, the produced graft is an autologous graft, made for example for a tooth previously extracted from the same patient. Optionally, the particles comprise a part of a bone graft, which may further include additional materials such as bone graft materials, for example including a titanium mesh. In some embodiments, the particulate form of the graft adapts to the shape of the bone in which the graft is implanted. Optionally, the plurality of particles are shaped to conform with a recess in the bone.

Figure 3:
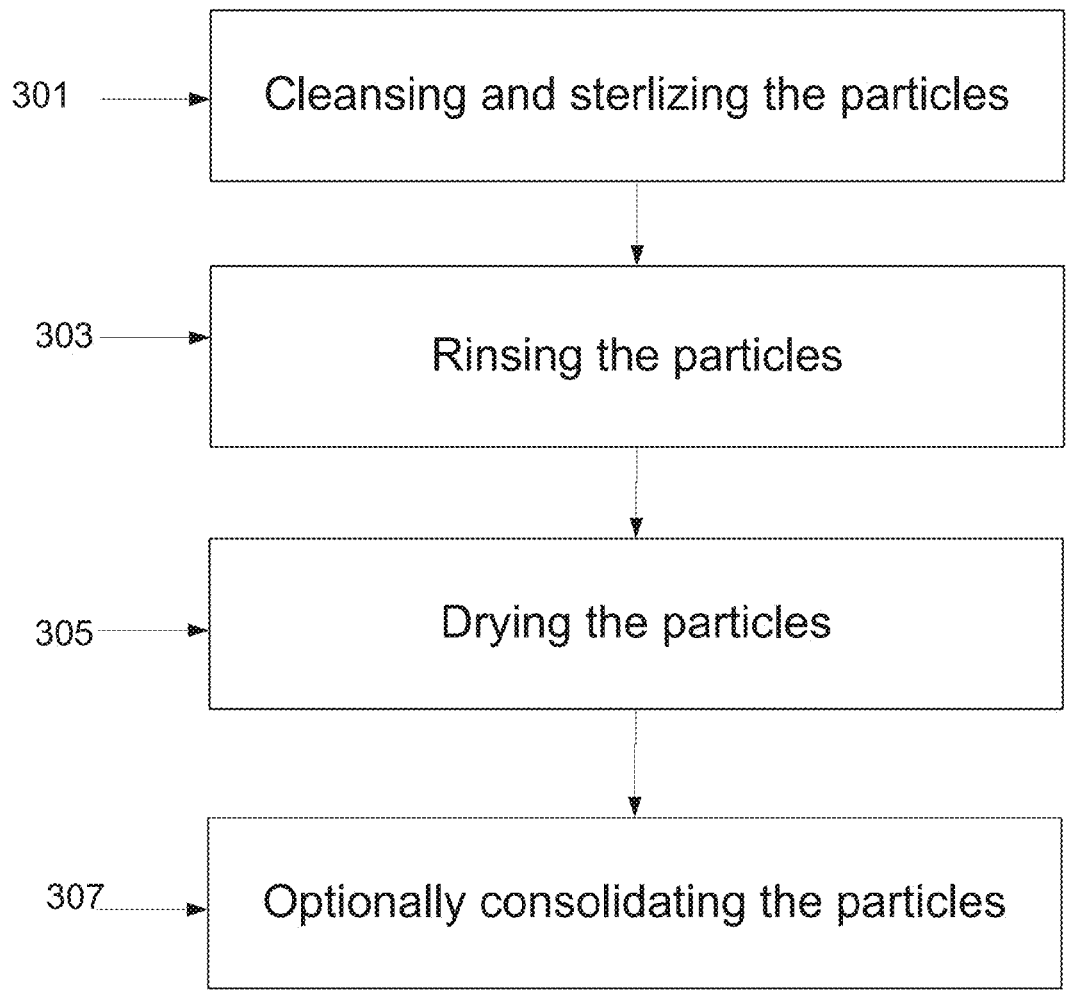
FIG. 3 is a flowchart of an exemplary process for preparing a plurality of tooth particles, according to some embodiments of the invention.

FIG. 3 is a flowchart of an exemplary process for preparing a plurality of tooth particles, according to some embodiments of the invention. In some embodiments, the selected subset of particles are prepared for implantation. In some embodiments, preparation procedures are selected to form a graft having chemical and/or physical properties similar to bone, and/or to bring the tooth particles into a configuration which better adapts to bone.

Optionally, preparing includes cleansing and sterilizing the particles (301), to remove organic debris and/or other contaminates, and/or obtain bacteria-free particles. Optionally, the particles are washed with a strong alkali, such as 0.25-0.75M of sodium hydroxide solution with 20-40% ethanol.

In some embodiments, the sterilized particles are rinsed (303). For example, the particles are washed with a PBS solution. Optionally, the rinsing solution causes a neutralizing reaction.

In some embodiments, the washed particles are dried (305). Optionally, the particles are dried using heating, for example by placing a container comprising the particles on a hot plate for several minutes. Optionally, the hot plate is set to a temperature of, for example, between 120-150 degrees Celsius, for example for 2-10 minutes. Additionally or alternatively, the particles are dried using air flow. Additionally or alternatively, the particles are left to dry over time in room temperature.

Optionally, the dried particles are united together, for example by addition of polymers such as polyglycolic, polylactic, silicum, fibrin, or non toxic cements. Optionally, the consolidated particles form a single piece, which can be shaped to conform to a recess in the bone in which the graft is implanted.

Figure 4:
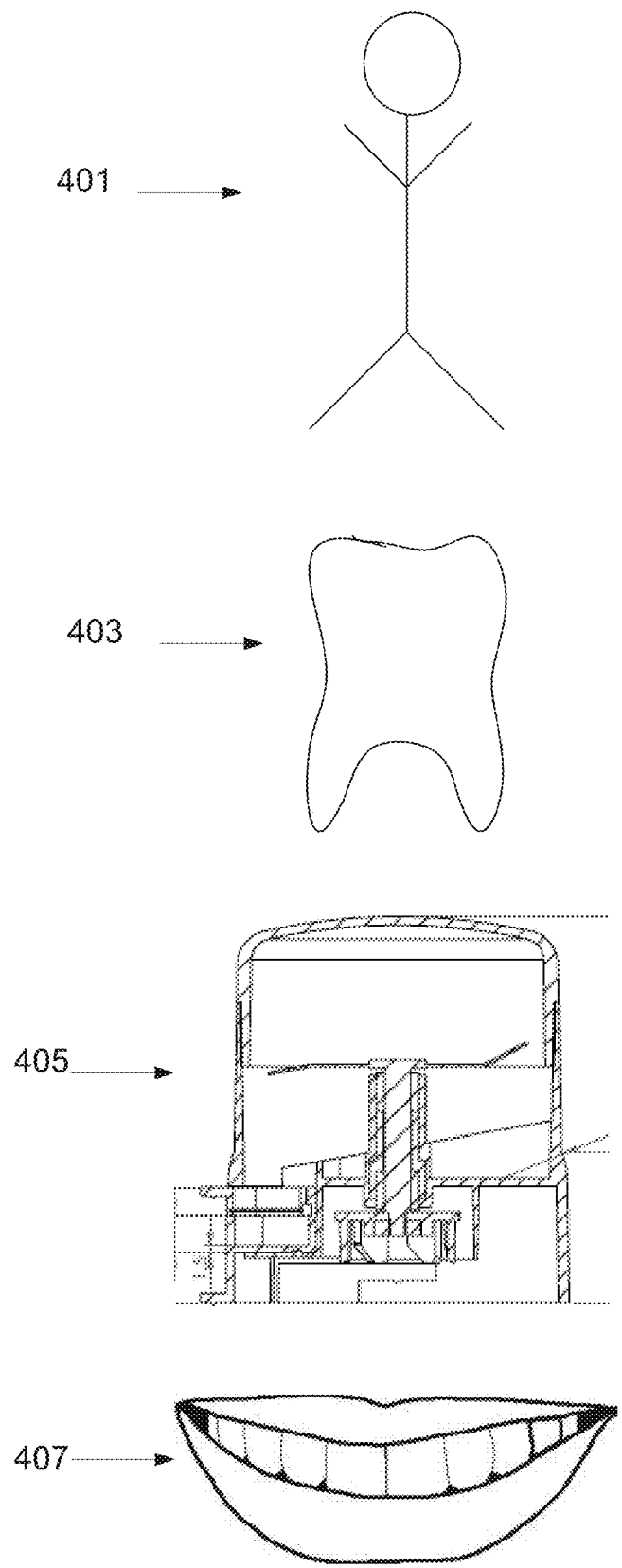
FIG. 4 is a flow diagram of an exemplary procedure for producing a bone graft at a dental clinic, according to some embodiments of the invention.

FIG. 4 is a flow diagram of an exemplary procedure for producing a bone graft at a dental clinic, according to some embodiments of the invention.

In some embodiments, a dentist 401 decides to prepare and implant a bone graft in a patient's mouth 407. In some embodiments, a tooth 403 is provided. Optionally, tooth 403 was previously extracted from the patient's mouth. Alternatively, tooth 403 is a cadaver tooth. Alternatively, tooth 403 is an animal tooth, such as porcine or cow tooth.

In some embodiments, to produce the graft, dentist 401 places tooth 403 within a table top device 405, for example at a tooth receiving chamber of the device, as will be further shown. Optionally, device 405 is configured for converting the tooth into a plurality of particles. Optionally, device 405 is configured for selecting a subset of particles to be used as a bone graft, for example by sifting the particles. Optionally, device 405 is configured for separating excess particles, which are optionally disposed. In some embodiments, device 405 automatically produces the graft from the provided tooth, for example upon the push of a button on a user interface of the device, for example by dentist 401.

In some embodiments, the produced graft is prepared for implantation, for example as explained hereinabove, and is then placed within the patient's mouth 407.

In some embodiments, the graft is produced within a time period ranging between, for example, 10 minutes to 1 hour, for example, 30 minutes, 20 minutes, 40 minutes from placing the tooth within device 405. Optionally, converting the tooth into particles and selecting a subset of particles is performed within, for example, a time period ranging between 10 seconds to 5 minutes, for example 12 seconds, 30 seconds, 1 minute, 4 minutes or intermediate, longer or shorter time periods, for example from providing the tooth. Optionally, preparation of the produced particles for implantation ranges between 5 minutes to 50 minutes, such as 10 minutes, 15 minutes, 25 minutes, or intermediate, longer or shorter time periods.

Figure 5:
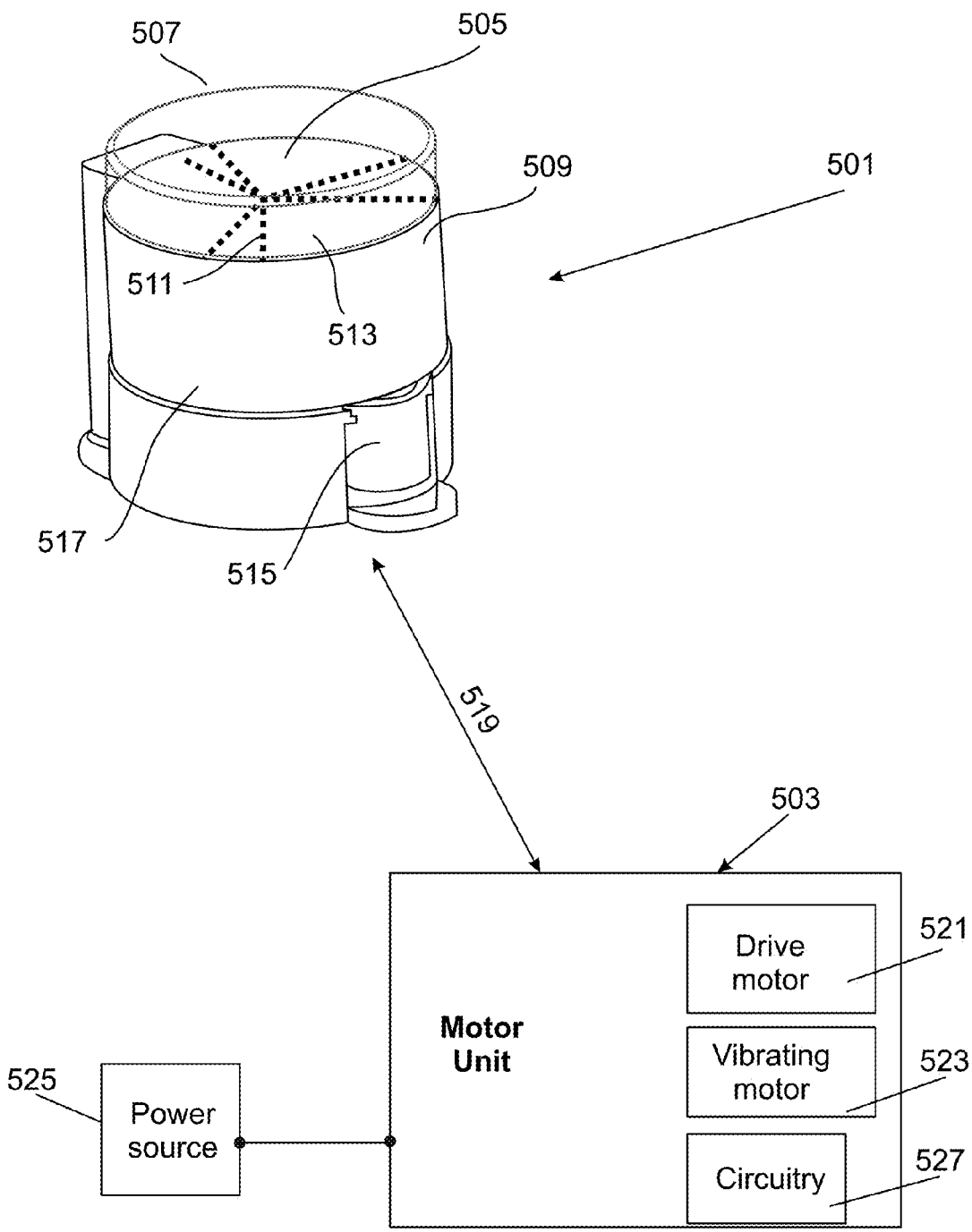
FIG. 5 is a diagram of a system for producing a dental bone graft, comprising a disposable unit and a permanent unit, according to some embodiments of the invention.

FIG. 5 is a diagram of a system for producing a dental bone graft, comprising a disposable unit 501 and a permanent unit 503, according to some embodiments of the invention.

In some embodiments, disposable unit 501 is configured for receiving a tooth, for example within a chamber 505 configured at a proximal end of housing 517 of the unit. Optionally, chamber 505 is covered by a lid 507. In some embodiments, lid 507 hermetically seals the chamber when closed. Optionally, lid 507 is transparent. Optionally, lid 507 can be partially lifted or removed, for example with the aid of a tab 509, for example to place the tooth within the chamber.

In some embodiments, a blade assembly comprising one or more blades 511 is configured within disposable unit 501, for example within chamber 505. Optionally, blades 511 are formed with one or more edges that are sharp enough to cut the tooth that is received within chamber 505. Additionally or alternatively, in some embodiments, chamber 505 includes other elements suitable for converting the tooth into particles, for example one or more blocks that are heavy enough to crush the tooth into particles.

Alternatively, in some embodiments, reusable blades are positioned within disposable unit 501. Optionally, the blades are detachable and can be reassembled in a different disposable unit, for example in the next use. Optionally, the reusable blades are sterilized between uses, for example in an autoclave.

In some embodiments, disposable unit 501 comprises one or more sieves, such as sieve 513. Optionally, the sieve is positioned distally to the blades, so that tooth particles obtained as a result of cutting the tooth fall onto sieve 513. In some embodiments, as will be further shown, additional one or more sieves are configured distally to sieve 513. Optionally, tooth particles pass between the sieves and a subset of selected particles is obtained.

In some embodiments, disposable unit 501 comprises one or more compartments, such as a particle receiving compartment 515. Optionally, compartment 515 is accessible to a user, for example it can be pulled out of and/or placed back into housing 517. In some embodiments, housing 517 includes one or more compartments for collecting the selected subset of particles, and/or one or more compartments for collecting excess particles. Optionally, the excess particles compartment(s) are removable from housing 517, for example to discard the excess particles.

In some embodiments, permanent unit 503 comprises one or motors. Optionally, a drive motor 521 is configured for moving blades 511, for example by rotating them. In some embodiments, unit 503 comprises a vibrating motor 523 configured for vibrating the one or more sieves and/or housing 517 of the disposable unit, for example to accelerate a sifting rate of the particles. Optionally, a single motor is configured for moving the blades as well as for causing vibration of the sieves and/or housing. In some embodiments, motor unit 503 is coupled to a power source 525, for example powered through a cable and socket connection to the electrical network, and/or powered by a portable power source such as batteries and/or a USB connection.

In some embodiments, motor unit 503 includes a seating on which disposable unit 501 is positioned. Optionally, disposable unit 501 and permanent unit 503 are coupled to each other through a connector 519. Optionally, connector 519 couples between a motor and blades 511, a motor and the sieves 513. In some embodiments, connector 519 includes a rotary shaft.

In some embodiments, motor unit 503 comprises circuitry 527. Optionally, the circuitry is configured for controlling one or more operational parameters, for example a rotation speed of the blades, an intensity of vibration, a duration of rotation and/or vibration, and/or other operational parameters. In some embodiments, permanent unit 503 comprises a user interface, for example configured as a button panel, through which a user may control operational parameters, activate and/or cease the graft production, and/or select an operational mode. Optionally, circuitry 527 is configured to provide one or more operational modes. Operational modes may be selected, for example, according to a size of the tooth to be converted, according to a number of teeth to be converted (for example in a situation in which more than one tooth such as 2, 3, 4, 5, teeth are used for forming the graft), according a desired level of grinding, according to future use of the graft (for example whether it is implanted or stored), or other parameters.

In some embodiments, disposable unit 501 is maintained in closed conditions during operation, such as to prevent contamination, for example due to covering by lid 507. Optionally, one or more protective elements, for example sterilizable bags or sheets are provided between chamber 505 and/or the one or more compartments such as compartment 515.

In some embodiments, disposable unit 501 is sterilized before packaging, and is packed in a sealed container to prevent contamination.

Optionally, permanent unit 503 is non-sterile. In some embodiments, connector 519 is configured for single use, and is shaped so that no direct contact is formed between disposable unit 501 and permanent unit 503 when they are coupled together, for example to prevent contamination to the disposable unit.

In some embodiments, housing 517 is coupled to a housing of the motor unit, for example by a mounting connection, a threaded connection, a projection and corresponding socket connection.

In some embodiments, a mechanism for limiting use of disposable unit 501 is provided. Optionally, the mechanism is mechanical, for example including a breakable pin which breaks when the disposable unit is coupled to the motor unit, preventing the disposable unit from re-engaging the motor unit a second time. Optionally, the mechanism includes a clasp or hinge which enable lifting lid 507 only a single time, to place the tooth inside chamber 505. Optionally, the mechanism includes a reader within permanent unit 503 which reads an identification code of disposable unit 501, allowing only a one-time coupling between the units.

In some embodiments, for example to ensure safe activation of the units when they are coupled together, lid 507 comprises a clasp or valve, which, in a situation in which lid 507 open, prevents activation of the motor unit. Optionally, when lid 507 is closed, the clasp or valve completes an electrical circuit, enabling activation of the motor(s).

Figure 6:
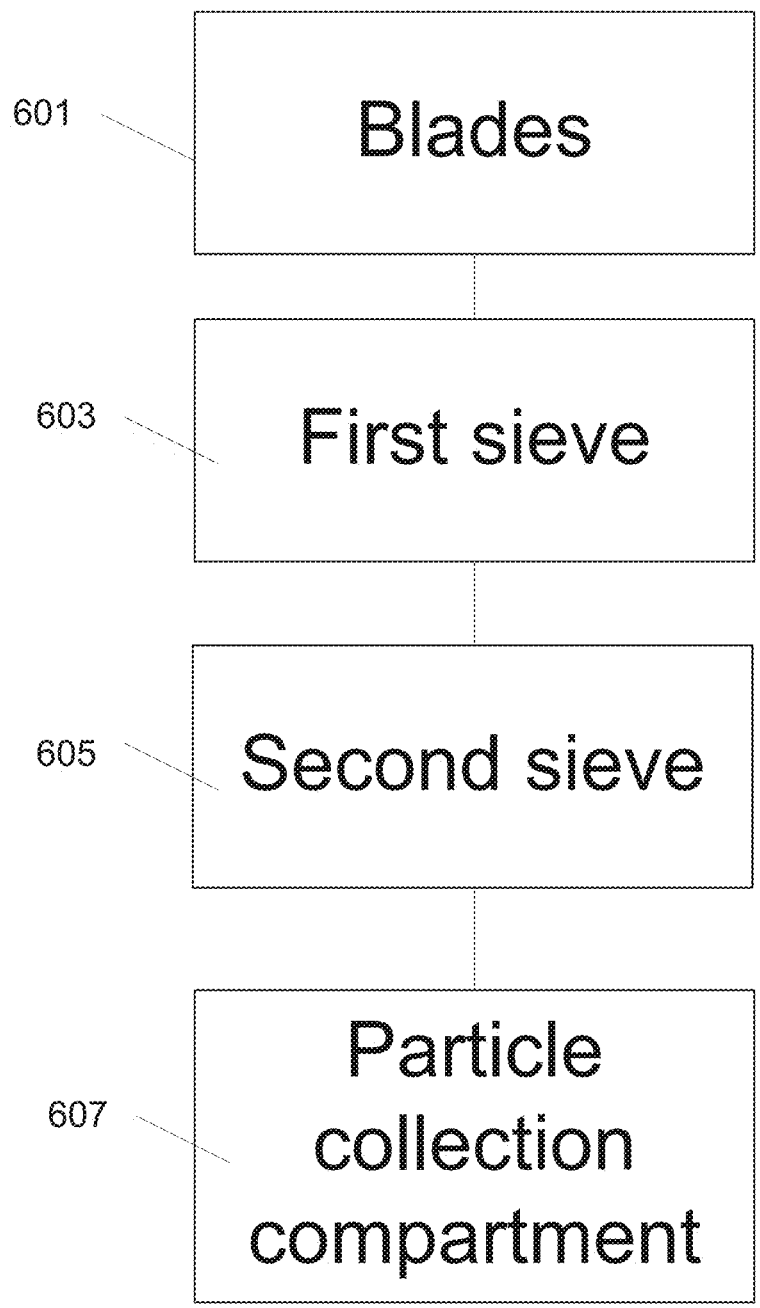
FIG. 6 is a diagram showing exemplary components of a disposable unit, according to some embodiments of the invention.

FIG. 6 is a diagram showing exemplary components of a disposable unit, according to some embodiments of the invention.

In some embodiments, for example as previously described herein, the disposable unit includes one or more blades (601).

In some embodiments, the disposable unit comprises a first sieve 603. Optionally, a bottom surface of a tooth receiving chamber of the device comprises one or more openings, and serves as the first sieve. Optionally, the first sieve is formed with openings sized to allow particles having a diameter smaller than, for example, 1200 µm, 1000 µm, 1500 µm, 2000 µm or intermediate, larger or smaller diameter to pass through. In some embodiments, the particles that passed the first sieve are collected within a compartment 607, for example positioned underneath the sieve. In some embodiments, a bottom surface of the collecting compartment comprises one or more openings, to serve as a second sieve 605. In some embodiments, the second sieve is formed with opening having a diameter smaller than, for example, 200 µm, 300 µm, 400 µm, or intermediate, larger or smaller diameters. In some embodiments, the second sieve is formed as a channel or slanted disc, onto which the particles fall from the first sieve. Optionally, the channel or disc is tilted to cause the particles to slide and/or roll down towards collection compartment 607.

In some embodiments, particles that were not selected, for example particles that did not pass through the first sieve for being too large and/or particles that passed the second sieve, therefore having a diameter too small to be used in a bone graft are collected within one or more compartments separated from compartment 607 in which the subset of particles to be used as a bone graft is collected. Optionally, the excess particles are disposed of. Alternatively, the large particles are placed again within the blades chamber, and are ground again into smaller particles. Additionally or alternatively, the small particles, which may comprise powder, are added to the selected subset of the particles at a later stage, for example added in during a consolidating process.

In some embodiments, sieve 603 and/or sieve 605 are vibrated, for example to accelerate a rate in which a portion of the particles pass through the sieves.

It is noted that the device may include any number of sieves, such as 1, 2, 3, 5, 6, 10 or intermediate, larger or smaller number, and that the one or more sieves are selected with a geometry (for example, openings) suitable to provide subsets of particles of various sizes.

It is noted that while the particles are referred to as having a diameter, it is clear that the particles may comprise various shapes other than spherical, for example the particles may comprise an arbitrary shape. A diameter is referred to herein for clarification purposes, for example for describing the process of selecting a subset of particles.

Figure 7:
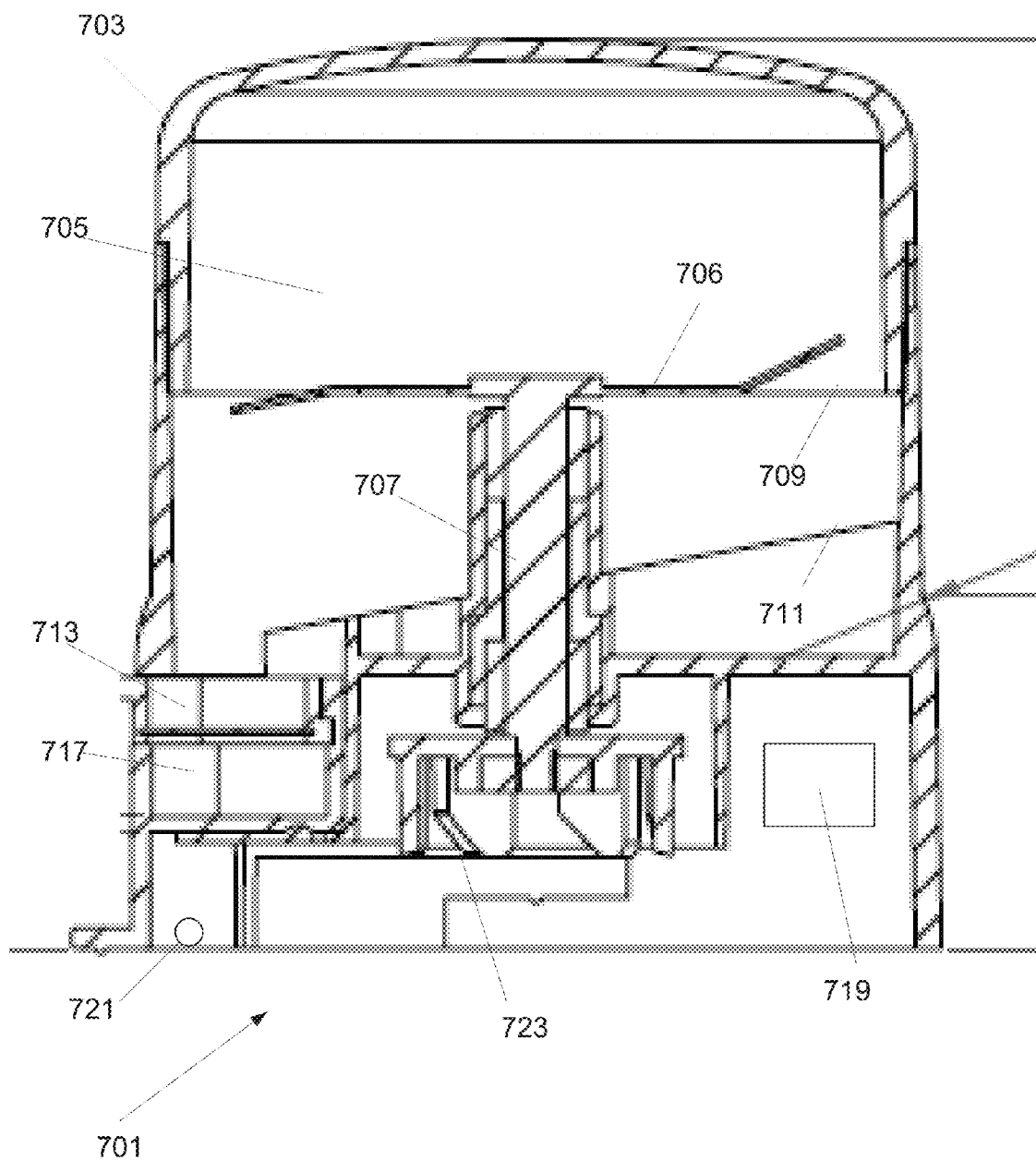
FIG. 7 is a drawing of an exemplary configuration of a disposable unit, according to some embodiments of the invention.

FIG. 7 is a drawing of an exemplary configuration of a disposable unit 701, according to some embodiments of the invention.

In some embodiments, housing 703 consists of a tooth receiving chamber 705, for example configured at a proximal end of the housing. A set of blades 706, for example, 1, 2, 3, 4, 5, 6, or larger number of blades are assembled within chamber 705. Optionally, blades 706 are coupled to a shaft 707, such as a rotary shaft configured for rotating the blades. Optionally, the blades are configured to rotate at a speed ranging between, for example, 10,000-20,000 RPM. Optionally, the blades are operated at a frequency ranging between, for example, 30-80 Hz. Optionally, a distal end of shaft 707 is coupled to a motor unit (not shown in this figure), which produces the rotation of blades 706.

In some embodiments, a first sieve 709 is positioned underneath blades 706. In some embodiments, a slanted surface 711 is positioned underneath sieve 709. Optionally, the slanted surface comprises openings for serving as an additional sieve.

In some embodiments, slanted surface 711 extends towards a first collection compartment 713. Optionally, particles that passed sieve 709 advance on surface 711, for example due to gravitational forces, and enter compartment 713. In some embodiments, a bottom surface 715 of compartment 713 comprises one or more openings, for sifting the particles again. Optionally, a portion of the particles that collected in compartment 713 fall into a second compartment 717.

In some embodiments, compartment 713 and/or compartment 717 are accessible to a user, for example they can be pulled out from and/or pushed back into housing 703, in a manner similar to opening and closing a drawer. Optionally, compartment 713 includes a selected subset of particles, and compartment 717 includes excess particles.

In some embodiments, disposable unit 701 comprises a vibrating element 719, for example configured as a weight. Optionally, the vibrating element is coupled to one or more sieves, to cause them to vibrate. Optionally, the vibrating element is configured to cause vibration of housing 703. Optionally, the vibrating element is causes vibration of the particles. Additionally or alternatively, blades 706 may weigh differently from each other, forming an asymmetrical configuration that causes vibration when rotated.

In some embodiments, disposable unit 701 comprises a sensor 721, configured for indicating a coupling between the motor unit and disposable unit 701. Optionally, the sensor is positioned at a surface of housing 703, for example a bottom surface, which is intended to engage the motor unit, so that the sensor senses contact between the units. Optionally, when there is no indication for a coupling between the units, the motor is inactivated.

In some embodiments, disposable unit 701 comprises a pin 723 which is caused to break and/or change positioning upon connecting between the disposable unit and the motor unit, and/or upon removal of the disposable unit from the motor unit, to prevent reuse of the disposable unit. Optionally, when pin 723 is broken or had changed its positioning, an alignment between the blade assembly and, for example, a rotary shaft which connects the blade assembly to the motor is interrupted, and inactivates rotation of the blades.

Figure 8:
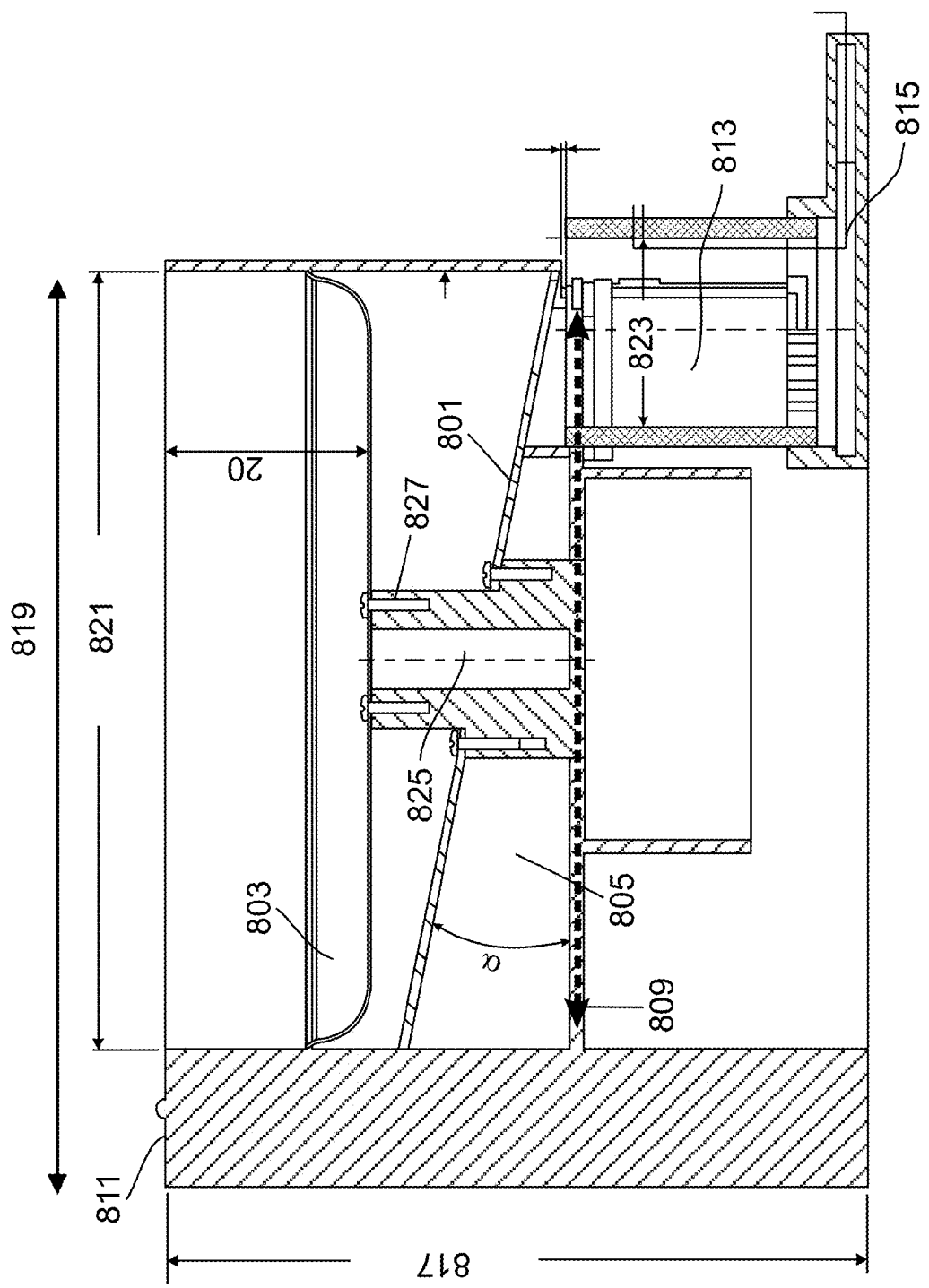
FIG. 8 is a drawing of another exemplary configuration of a disposable unit, according to some embodiments of the invention.

FIG. 8 is a drawing of another exemplary configuration of a disposable unit, according to some embodiments of the invention. In this configuration, a slanted disc 801 is positioned distally to a first sieve 803. Optionally, disc 801 comprises one or more openings 807, causing at least a portion of the particles to pass into lumen 805, for example as the flow of particles advances on surface of disc 801.

In some embodiments, disc 801 is positioned at an angle α with respect to horizontal axis 809 extending between the side walls of housing 811. Optionally, angle α ranges between, for example 3-40 degrees, such as 5 degrees, 11 degrees, 20 degrees, 30 degrees, or intermediate, larger or smaller angles.

In some embodiments, a lower end of disc 801 leads to a collection compartment 813. Optionally, compartment 813 comprises a cylindrical shape, for example having a diameter 823 ranging between 10-30 mm, such as 15 mm, 19 mm, 25 mm. In some embodiments, compartment 813 is attached at its distal end to a base 815. Optionally, base 815 extends beyond a periphery of housing 811, for example to facilitate removal of compartment 813 from housing 811.

Exemplary dimensions of housing 811 may include a height 817 ranging between 40-150 mm, a width 819 (or, in some embodiments, diameter) ranging between 50-200 mm.

In some embodiments, a diameter 821 of sieve 803 ranges between 50-120 mm Optionally, a diameter of sieve 803 is similar to a width (in some embodiments, diameter) 819 of housing 811.

In some embodiments, disc 801 and sieve 803 are connected a shaft 825, for example configured for coupling the disposable unit to a motor unit, by one or more fixation screws 827. Additionally or alternatively, these components or other components of the disposable unit may be coupled to each other by a mounting, or any other type of attachment.

FIGS. 9A-D are drawings of a particle collection compartment, according to some embodiments of the invention.

Figure 9A:
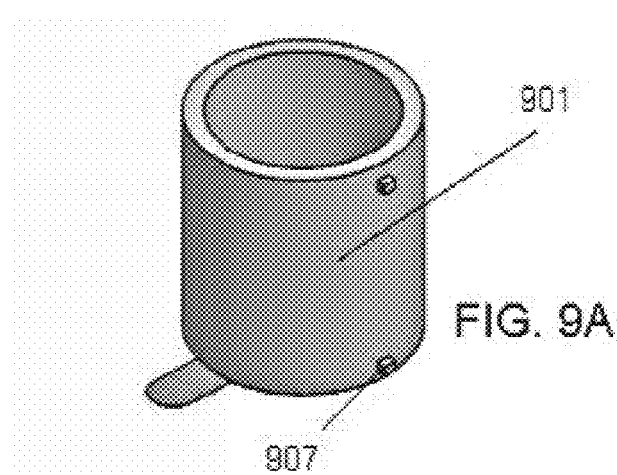
FIGS. 9A-D are drawings of a particle collection compartment, according to some embodiments of the invention.
Figure 9B:
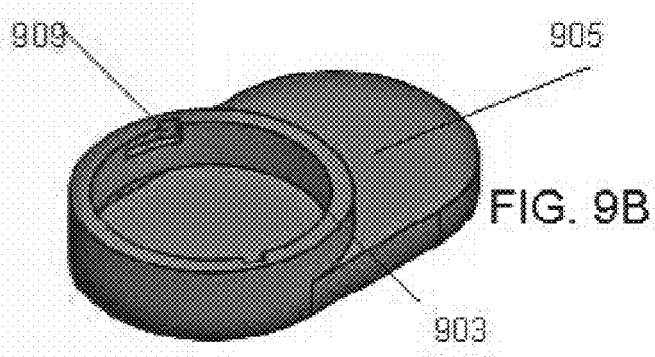
Figure 9C:
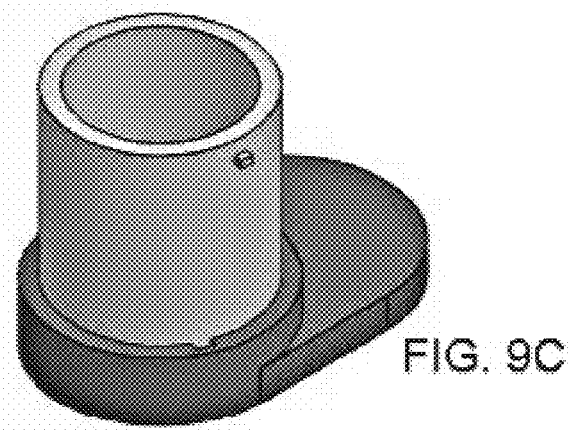
Figure 9D:
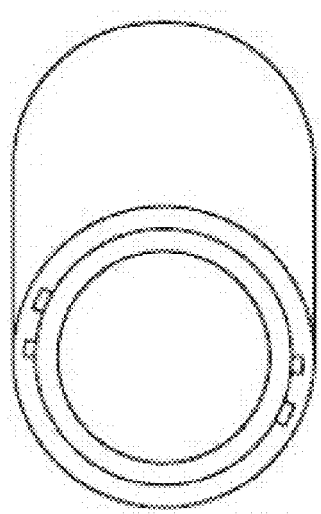

FIG. 9A shows a cylindrical compartment 901 for collecting tooth particles, according to some embodiments of the invention. FIG. 9B shows a base 903 on which compartment 901 is positioned, according to some embodiments of the invention. FIG. 9C shows an assembly of a collection compartment 901 and a base 903, according to some embodiments of the invention. FIG. 9D shows a top view of the compartment and base assembly, according to some embodiments of the invention.

In some embodiments, compartment 901 and/or base 903 comprise an extension 905, for example shaped as a rounded tab, which extends beyond a housing of the disposable unit, for example to facilitate removal of the collection compartment from the housing, when it has been filled with particles.

In some embodiments, compartment 901 is configured to lock onto base 903. A potential advantage of locking may include preventing movement and/or removal of the compartment, for example during activation of the device, such as activation of a motor. In some embodiments, compartment 901 comprises one or more projections 907, extending for example radially outwardly from compartment 901. Optionally, base 903 comprises one or more indentations 909, shaped and/or sized to receive projections 907. In some embodiments, when positioning compartment 901 on top of base 903, projections 907 and corresponding indentations 909 are used for orienting compartment 901. Optionally, by positioning compartment 901 on base 903 and rotating the compartment, the projections slide into a locked position, for example as shown in FIG. 9D, to prevent compartment 901 from disengaging base 903.

In some embodiments, compartment 901 comprises a sieve (not shown in this figure). Optionally, the sieve is a second sieve, for example in addition to a first sieve configured at a tooth receiving chamber. In some embodiments, the sieve is located in proximity to the bottom of compartment 901. Optionally, the sieve is sized to allow particles of less than 300 μm, less than 200 μm, less than 400 μm or intermediate, higher or smaller diameters to pass through. Optionally, particles of a larger diameter, for example ranging between 300-1200 μm accumulate on a top surface of the sieve. A user may then access the sieve, for example by drawing it out of the compartment, and collect the particles, for example with the help of a syringe.

Figure 10A:
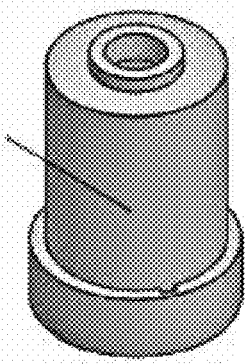
FIGS. 10A-E are drawings of a connector for coupling between a disposable unit and a permanent unit, according to some embodiments of the invention.
Figure 10B:
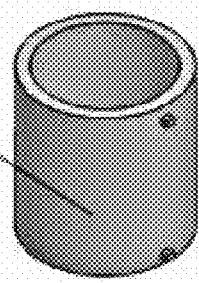
Figure 10C:
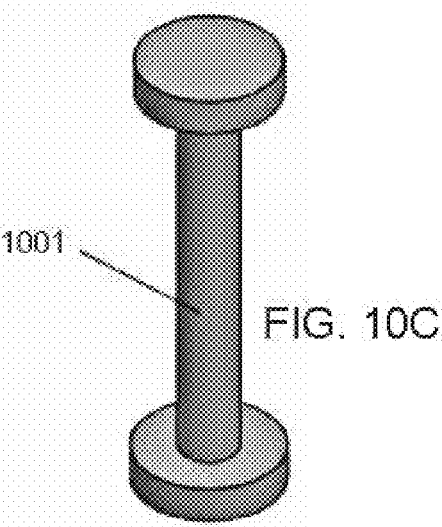
Figure 10D:
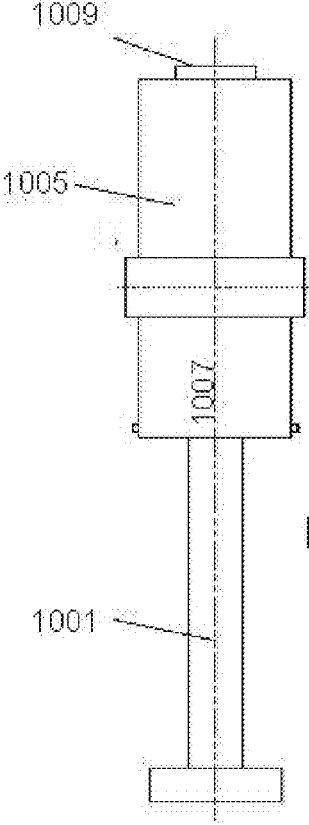
Figure 10E:
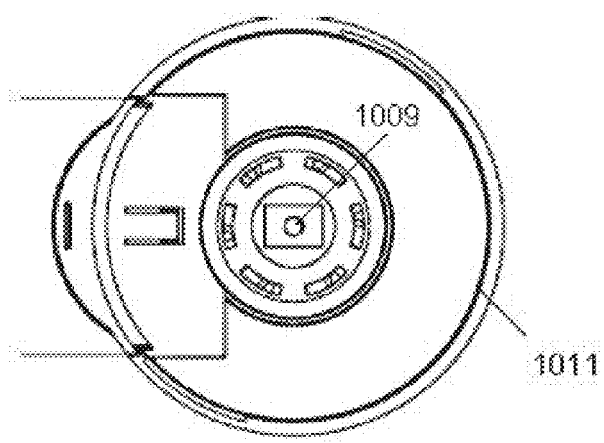

FIGS. 10A-E are drawings of a connector for coupling between a disposable unit and a permanent unit, according to some embodiments of the invention. In some embodiments, the connector is formed as a rotary shaft 1001, as shown for example in FIG. 10C. Optionally, shaft 1001 is received within a cylindrical shaft 1003, as shown in FIG. 10B. Optionally, an assembly of rotary shaft 1001 and cylindrical shaft 1003 is fitted within a housing 1005, forming a connector for example as shown in FIG. 10D. Optionally, a proximal portion of the connector is coupled to a disposable unit, for example connected to a set of blades (not shown in this figure), and a distal portion of the connector is coupled to a motor unit. Optionally, the connector is assembled such that its longitudinal axis 1007 unites with a longitudinal axis of the disposable unit. FIG. 10E shows a top view of a disposable unit, wherein proximal end face 109 of the connector is shown at the center of the unit. Alternatively, the connector is positioned in other configurations, for example extending longitudinally along the walls of housing 1011 of the disposable unit, or extending externally to housing 1011 for example in a radially outward direction.

Figure 11:
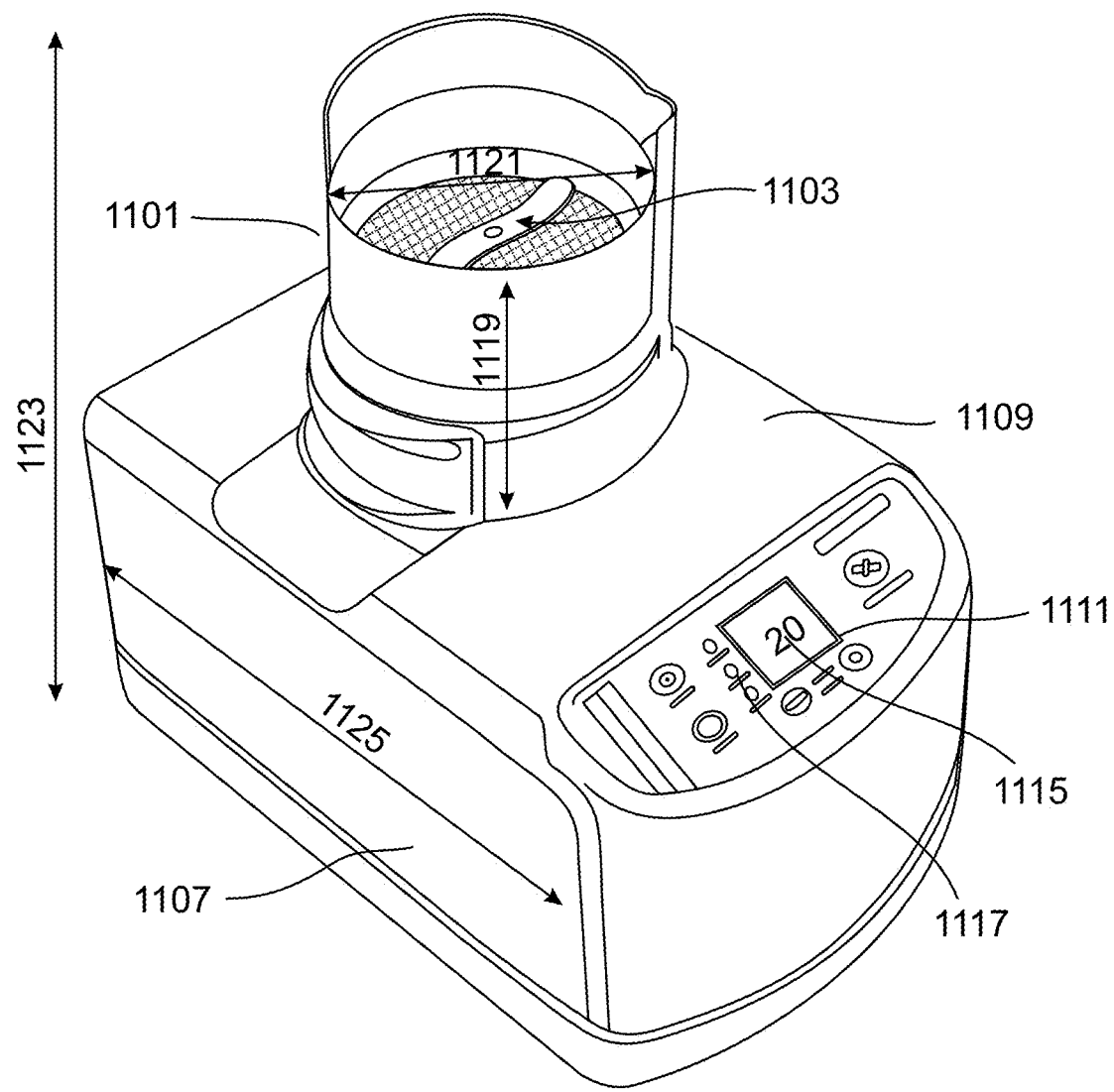
FIG. 11 is a photo of a table top device for converting a tooth into a bone graft, according to some embodiments of the invention.

FIG. 11 is a photo of a table top device for converting a tooth into a bone graft, according to some embodiments of the invention.

A disposable unit 1101 comprising a set of blades 1103 and one or more sieves 1105 is positioned on top of a permanent motor unit 1107. In some embodiments, a housing 1109 of motor unit 1107 comprises a user interface, for example in the form of a button panel 1111. Optionally, the button panel 1111 comprises an on/off button. Optionally, the button panel 1111 comprises a screen 1115 for indicating and/or setting a duration of operation, for example showing the time left until the conversion of the tooth into particles and/or the sifting process is complete. Optionally, panel 1111 comprises one or more light indications 1117 to show a current status or operational mode. Optionally, panel 1111 comprises one or more buttons for modifying a rate of conversion and/or sifting. Optionally, panel 1111 comprises a button for activating and/or ceasing vibration.

Exemplary materials of disposable unit 1101 may include: a housing formed of, for example, plastic, titanium or titanium alloys, stainless steel; blades formed of, for example, metal, such as stainless steel, titanium or titanium alloys, zirconium, palladium; one or more sieves formed of, for example, plastic, titanium, silk, polymers.

Exemplary dimensions and measures of disposable unit 1101 may include a height 1119 ranging between 80-120 mm, a diameter 1121 ranging between 60-100 mm, a weight ranging between 150-250 gr.

Exemplary dimensions and measures of the table top device including disposable unit 1101 and permanent unit 1107 may include a height 1123 ranging between 150-250 mm, a maximal width 1125 ranging between 100-150 mm, a weight ranging between 1000-2000 gr.

Figure 12:
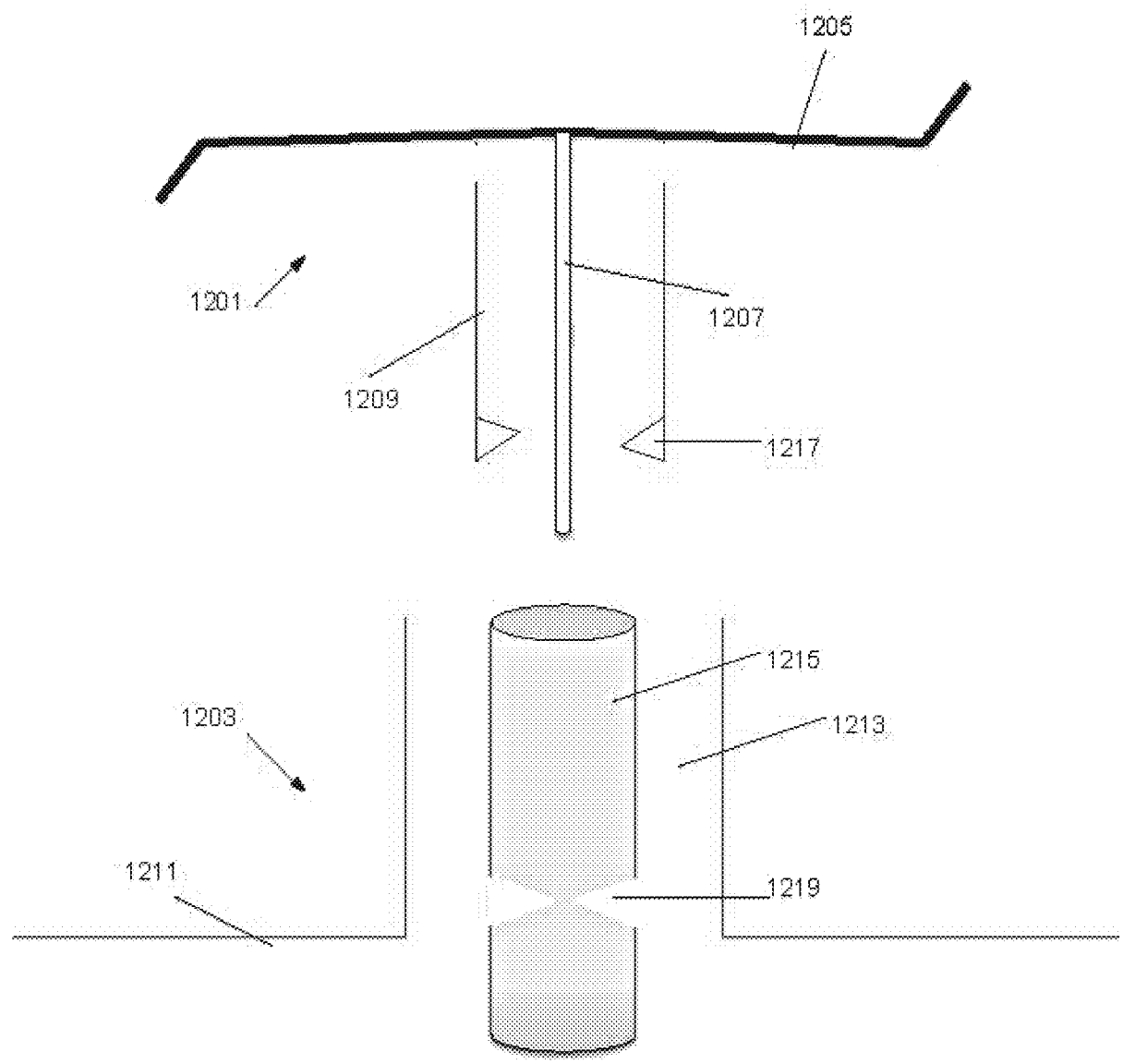
FIG. 12 is an exemplary configuration for a coupling between a disposable unit and a permanent unit, according to some embodiments of the invention.

FIG. 12 shows an exemplary coupling configuration for connecting between a blade assembly 1201 of a disposable unit, and a motor unit 1203. In some embodiments, blades 1205 are connected to a rod 1207, configured for rotating the blades. Optionally, a hollow shaft 1209 surrounds rod 1207. Optionally, shaft 1209 is sized and/or shaped to fit within housing 1211 of motor unit 1203, for example in a cylindrical bore 1213, as shown in this figure. In some embodiments, a cannulated shaft 1215 is positioned within bore 1213, sized and/or shaped to receive rod 1207 within a longitudinally extending lumen formed within the shaft. Optionally, shaft 1215 is sized and/or shaped to co-centrally fit within hollow shaft 1207. In some embodiments, shaft 1209 comprises one or more projections 1217, and shaft 1215 comprises one more respective recesses 1219 that receive the projections. Optionally, during coupling of the blade assembly to the motor unit, the projections and respective recesses provide a locking connection between shaft 1215 and shaft 1209. Optionally, rod 1207 passes along a central longitudinal axis of the shafts, and is configured to be rotated by the motor to cause rotation of the blades.

As used herein the, the terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of producing a bone autograft, comprising:
   providing one or more teeth;
   providing a table top apparatus comprising:
      a housing encasing:
         a chamber sized to receive said one or more teeth;
         a blade assembly positioned within said chamber and configured to pulverize said one or more teeth;
         an accessible compartment in which a subset of tooth particles is collected; and
         a plurality of sieves positioned to sift particles that flow between said chamber and said accessible compartment, said sieves comprising
            at least a first sieve sized to pass particles having a diameter which is substantially smaller than a first threshold, and a second sieve sized to pass particles having a diameter which is substantially smaller than a second threshold;
   converting, using said blade assembly said one or more teeth into a plurality of particles;
   selecting, using said plurality of sieves, a subset of particles selected from said plurality of particles to produce said autograft.

2. The method according to claim 1, wherein said converting and selecting are performed at a dental clinic within a time period shorter than one hour from extraction of said one or more teeth from said subject.

3. The method according to claim 1, wherein a minimal diameter of at least 70% of the particles of said subset of particles is substantially 200 μm or more, and wherein a maximal diameter of at least 70% of the particles of said subset of particles is substantially 1200 μm or less.

4. The method according to claim 1, further comprising grafting said autograft in a jaw of said subject.

5. The method according to claim 4, wherein said converting, selecting and grafting is performed within a time limit of 30 minutes.

6. The method according to claim 1, wherein said converting comprises rotating said blade assembly at a speed of at least 10,000 RPM for pulverizing said one or more teeth into said plurality of particles.

7. The method according to claim 1, comprising at least one of: vibrating one or more of said plurality of sieves, vibrating said housing, and vibrating the particles themselves.

8. The method according to claim 1, further comprising adding treatment fluid to said subset of particles, said treatment fluid comprising sterilizing fluid suitable for removing organic debris from said subset of particles.

9. The method according to claim 8, wherein said treatment fluid is cleansing fluid and said organic debris comprises one or more of bacteria, viruses and endotoxins.

10. The method according to claim 1, further comprising drying said particles.

11. The method according to claim 1, wherein said converting comprises converting a whole tooth or portions of a tooth into said particles.

12. The method according to claim 11, wherein said whole tooth or portions of a tooth comprise at least one of dentin and enamel.

13. The method according to claim 1, further comprising adding to said subset of particles one or more substances from: antibiotics, bisphosphonates, blood or blood components, bone growth inducing materials.

14. The method according to claim 1, further comprising, prior to said converting, processing said tooth to remove toxins.

15. A table top apparatus configured for connecting to a motor unit to produce a bone autograft at a dental clinic, comprising:
 a housing encasing:
 a chamber sized to receive one or more teeth;
 a blade assembly positioned within said chamber and configured to pulverize said one or more teeth;
 an accessible compartment in which a subset of tooth particles is collected; and
 a plurality of sieves positioned to sift particles that flow between said chamber and said accessible compartment, said sieves comprising at least a first sieve sized to pass particles having a diameter which is substantially smaller than a first threshold, and a second sieve sized to pass particles having a diameter which is substantially smaller than a second threshold.

16. The apparatus according to claim 15, wherein said first threshold is 1200 μm, and said second threshold is 200 μm.

17. The apparatus according to claim 15, wherein said second sieve is positioned at an angle ranging between 3-40 degrees, forming a slanted surface on which said particles are advanced towards said accessible compartment.

18. The apparatus according to claim 15, wherein said first sieve is configured vertically below said blades, and said second sieve is configured vertically below said first sieve, so that said flow of particles is driven by gravity.

19. The apparatus according to claim 15, wherein said apparatus is packaged in a sealed container to maintain a sterile environment.

20. The apparatus according to claim 15, wherein dimensions of said apparatus include a height shorter than 250 mm, and a width shorter than 150 mm.

21. The apparatus according to claim 15, wherein said accessible compartment is configured below said sieves and is accessible from a side wall of said housing.

22. The apparatus according to claim 15, wherein a weight of said apparatus is less than 2000 grams.

23. A kit comprising:
 The apparatus according to claim 15; and a motor unit operably connectable to said apparatus.

24. The apparatus according to claim 23, further comprising a connector comprising a rotary shaft for coupling said apparatus to said motor unit.

25. The kit according to claim 23, wherein at least one of said motor unit and said apparatus comprises a vibrating module configured to vibrate one or more of said sieves, said housing, or said particles.

26. The kit according to claim 23, wherein at least one of said apparatus and a connector of said apparatus and said motor unit comprises a mechanism for preventing reuse of said apparatus.

27. The kit according to claim 26, wherein said motor unit comprises a reader configured to recognize an identification code on said apparatus.

28. The kit according to claim 26, wherein at least one of said motor unit and said apparatus comprises a breakable pin which prevents the apparatus from engaging the motor unit a second time.

29. The kit according to claim 23, wherein said motor unit comprises circuitry configured for controlling parameters of at least one of pulverizing said one or more teeth and sifting said particles, said parameters comprising one or more of an RPM of said blades, an intensity of vibration of said sieves, a duration of grinding.

30. The kit according to claim 29, wherein said motor unit further comprises a user interface comprising at least one of a button panel and a screen for selecting said parameters and activating said circuitry.

31. The kit according to claim 23, wherein said motor unit is disposed underneath said blade assembly.

* * * * *